(12) United States Patent
Sato (10) Patent No.: US 9,322,802 B2
(45) Date of Patent: Apr. 26, 2016

(54) APPARATUS FOR DETECTING CHEMICAL SUBSTANCES

(75) Inventor: Tomoyoshi Sato, Ibaraki (JP)

(73) Assignee: ATONARP INC., Tokyo (JP)

( * ) Notice: Subject to any disclaimer, the term of this patent is extended or adjusted under 35 U.S.C. 154(b) by 979 days.

(21) Appl. No.: 13/517,067

(22) PCT Filed: Dec. 22, 2010

(86) PCT No.: PCT/JP2010/007455
§ 371 (c)(1),
(2), (4) Date: Aug. 22, 2012

(87) PCT Pub. No.: WO2011/077731
PCT Pub. Date: Jun. 30, 2011

(65) Prior Publication Data
US 2012/0319863 A1  Dec. 20, 2012

(30) Foreign Application Priority Data

Dec. 22, 2009 (JP) ................. 2009-291001

(51) Int. Cl.
 G08C 15/06 (2006.01)
 G01N 27/62 (2006.01)
(52) U.S. Cl.
 CPC .................... *G01N 27/622* (2013.01)
(58) Field of Classification Search
 CPC ............ G01N 27/622; G01N 1/2273; G01N 2001/022; G01N 2021/1734; G01N 2021/1795; G01N 2021/3513; G01N 2021/394; G01N 21/3504; G01N 27/624; G01D 4/004; H04Q 9/00; Y02B 90/242; Y04S 20/322; G01F 15/063; A61K 2039/505; A61K 39/3955; A61K 41/0004
 See application file for complete search history.

(56) References Cited

U.S. PATENT DOCUMENTS

| 5,440,916 A * | 8/1995 | Stone | B25J 19/0079 73/23.31 |
| 5,541,851 A * | 7/1996 | Sato | G01N 33/0031 700/266 |
| 7,034,677 B2 * | 4/2006 | Steinthal | B82Y 30/00 128/903 |

(Continued)

FOREIGN PATENT DOCUMENTS

| JP | 2002539446 A | 11/2002 |
| JP | 2008512689 A | 4/2008 |

(Continued)

OTHER PUBLICATIONS

English Translation of International Preliminary Report for Application No. PCT/JP2010/007455 dated Aug. 9, 2012.

(Continued)

*Primary Examiner* — Amine Benlagsir
*Assistant Examiner* — Sisay Yacob
(74) *Attorney, Agent, or Firm* — Buchanan Ingersoll & Rooney PC (57) ABSTRACT

An olfactory system (300) capable of detecting a threat includes: a detection unit (100) including an IMS sensor (110) that outputs IMS data (115) relating to chemical substances included in fluid at a sampling point; a local memory (41) storing a library (49) including a specifying pattern (48) generated when a specified chemical substance was detected by the IMS sensor (110); and a matching unit (42) that routinely compares and matches the IMS data (115) and the specifying pattern (48) for monitoring purposes included in the library (49).

10 Claims, 3 Drawing Sheets

(56) References Cited

U.S. PATENT DOCUMENTS

| | | | |
|---|---|---|---|
| 7,337,686 B2 * | 3/2008 | Sagi-Dolev | G01N 35/0099 340/521 |
| 7,684,966 B1 * | 3/2010 | Genovese | G06Q 10/00 700/83 |
| 2006/0024307 A1 | 2/2006 | Epshteni et al. | |
| 2009/0055102 A1 | 2/2009 | Laufer et al. | |
| 2009/0097020 A1 * | 4/2009 | Treado | G01N 21/64 356/301 |
| 2009/0132177 A1 | 5/2009 | Arnold | |
| 2010/0001182 A1 | 1/2010 | Burchfield et al. | |
| 2010/0148946 A1 * | 6/2010 | Strombeck | G08B 25/10 340/425.5 |

FOREIGN PATENT DOCUMENTS

| | | |
|---|---|---|
| JP | 2008517276 A | 5/2008 |
| JP | 2008527396 A | 7/2008 |
| JP | 2009002815 A | 1/2009 |
| JP | 2009541924 A | 11/2009 |
| WO | WO-00/55602 A1 | 9/2000 |
| WO | WO-2005/052546 A2 | 6/2005 |
| WO | WO-2006/013396 A2 | 2/2006 |
| WO | WO-2008/039996 A2 | 4/2008 |

OTHER PUBLICATIONS

International Search Report from corresponding International Application No. PCT/JP2010/007455 mailing date Feb. 22, 2011.

* cited by examiner

APPARATUS FOR DETECTING CHEMICAL SUBSTANCES

TECHNICAL FIELD

The present invention relates to an apparatus that detects chemical substances using a sensor.

BACKGROUND ART

WO2006/013396 (Japanese Patent Publication No. 2008-508693) discloses an ion mobility spectrometer with an ion filter in the form of at least one ion channel that includes a plurality of electrodes. WO2005/052546 (Japanese Patent Publication No. 2007-513340) discloses an ion mobility-based system, method, and apparatus for analyzing samples.

DISCLOSURE OF THE INVENTION

The ability to respond to situations that require prompt action, such as the presence of hazardous substances, like explosives, poisons, and poisonous gases, is important.

One aspect of the present invention is an apparatus including: a detection unit acquiring chemical substance-related information relating to chemical substances included in a fluid at a sampling point using a first type of sensor; a local memory storing a library including a specifying pattern generated when a specified chemical substance was detected by the first type of sensor; and a matching unit that routinely compares the chemical substance-related information obtained by the detection unit and a specifying pattern for monitoring purposes included in the library and outputs match information when the obtained chemical substance-related information and the specifying pattern for monitoring purposes match. The number of varieties of chemical substances that can be the cause of a threat that needs immediate detection is not so large. Accordingly, by storing specifying patterns, which can be directly compared with the output of the first type of sensor used to detect chemical substances, in a local memory such as a cache memory which has a short access time, it is possible to determine the probability of a threat occurring in a short time.

A typical example of the first type of sensor is a spectrometric sensor that outputs the chemical substance-related information as a spectrum (waveform data), and the specifying pattern includes spectral features (waveform characteristics, spectral characteristics, a spectral signature). A typical example of a spectrometric sensor is an ion mobility sensor. The matching unit (collation unit) carries out matching or collation for a spectrum obtained from the spectrometric sensor using spectral features included in a specifying pattern. The matching unit may extract spectral features from the obtained spectrum or may synthesize a spectrum for matching purposes from the spectral features.

With this apparatus, when an event output unit that outputs an occurrence of an event and an occurrence cause of the event according to a change in the obtained chemical substance-related information is also included, the matching unit should preferably operate in parallel with, or according to time division or time share with, the event output unit. It is not problematic if some time is required to determine whether an event that does not pose a threat has occurred and there are a vast number of occurrence causes for such events. Accordingly, the processing that determines (estimates) the occurrence cause of such an event is defined as processing that differs to discovery of the cause of the extremely limited number of threats, and by carrying out such processing according to time division or in parallel, it is possible to routinely determine the presence of a cause of a threat in a short time.

This apparatus may further include a communication unit that communicates with the outside wirelessly or using wires, and the event output unit may transfer event occurrence information including the chemical substance-related information to the outside and acquire the occurrence cause of the event via the communication unit. Even during communication with the outside using the communication unit, it is possible to routinely determine or judge the probability of a cause of a threat being present using the matching unit.

The apparatus should preferably also include an automated updating unit that automatically updates the specifying pattern or patterns stored in the library of the local memory via the communication unit. By storing specifying patterns relating to the causes of threats that have a high probability of occurring in the library, it is possible to determine or find the probability of the cause of a threat being present much more reliably.

The automated updating unit can update the specifying patterns based on the occurrence cause of the event. Also, if the apparatus further includes a unit that acquires event appended information including images and/or sound around or surrounding the apparatus, the automated updating unit can update the specifying patterns based on the event appended information.

The apparatus may also further include a sample storing unit that seals the fluid at the sampling point in a storage capsule. When the occurrence cause of the event is not established or the like, by storing the fluid at the sampling point, analyzing the chemical substances included in the fluid at another analyzer, and registering a specifying pattern of the first type of sensor for such chemical substances in the database, it is possible to add to a knowledge database of causes of threats and/or occurrence causes of events.

Another aspect of the present invention is a method that controls an apparatus including a detection unit detecting chemical substance-related information relating to chemical substances included in a fluid at a sampling point using a first type of sensor, the method including the following steps.

1. Having a library including a specifying pattern generated when a specified chemical substance was detected by the first type of sensor stored in the local memory of the apparatus, and routinely comparing chemical substance-related information obtained by the detection unit and a specifying pattern for monitoring purposes included in the library.

2. Outputting match information when the obtained chemical substance-related information and the specifying pattern for monitoring purposes match.

This method should preferably also include the following step.

3. Outputting an occurrence of an event and an occurrence cause of the event according to a change in the obtained chemical substance-related information.

In this case, the step of outputting of match information in step 2 is carried out in parallel with, or according to time division (time sharing) with the step of outputting an occurrence cause in step 3. The step of outputting occurrence cause in step 3 may include transferring event occurrence information including the obtained chemical substance-related information to the outside and acquiring the occurrence cause of the event via a communication unit that communicates with the outside wirelessly or using wires. The specifying patterns stored in the library of a local memory may be automatically updated via the communication unit. The specifying patterns may be updated based on the occurrence cause of an event or may be updated based on the event appended information including images and/or sound around or neighboring or the apparatus.

Yet another aspect of the present invention is a program (or program product) executed by an apparatus including a detection unit detecting chemical substance-related information relating to chemical substances included in a fluid at a sampling point using a first type of sensor, a CPU, and a memory, the program including instructions for executing the control described above. Such program (program product) may be provided having been recorded on a recording medium (such as an optical disc) or may be provided via a computer network such as the Internet.

DETAIL DESCRIPTION

Figure 1:
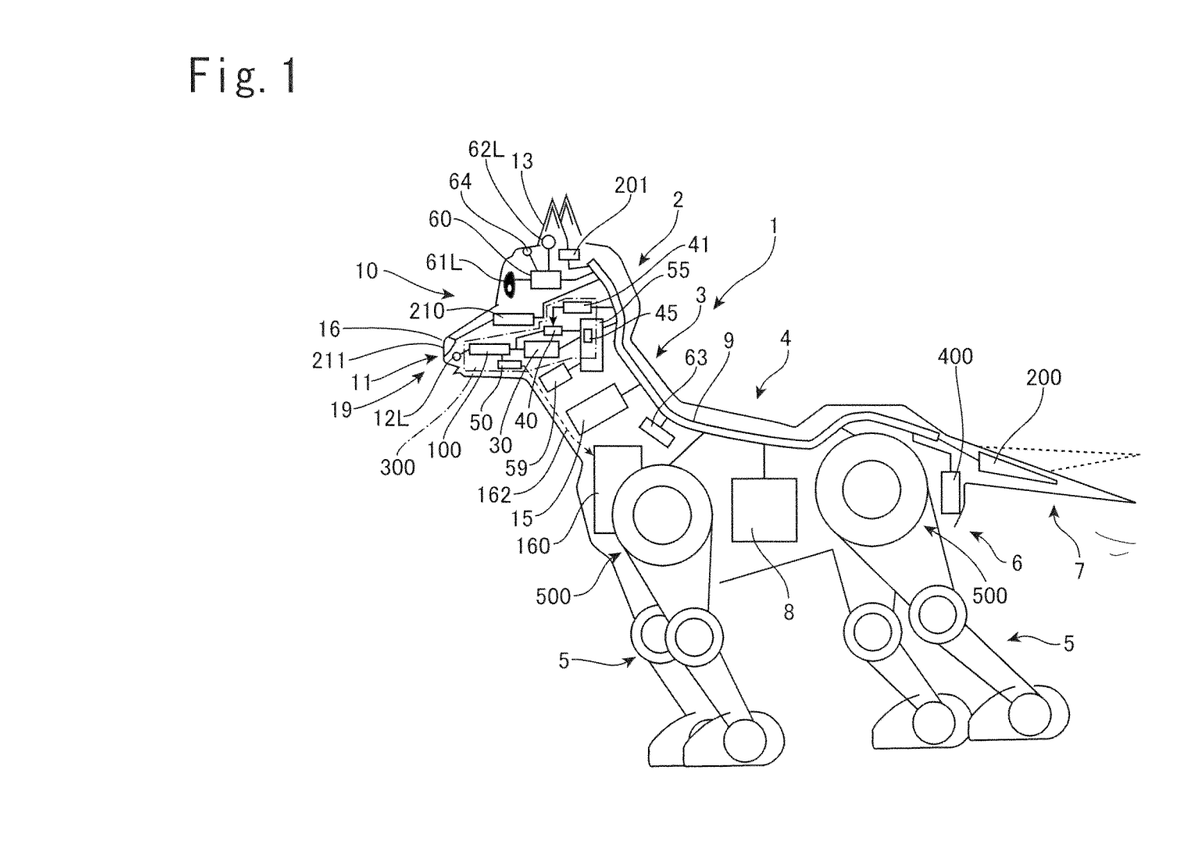
FIG. 1 is a block diagram showing the arrangement of a robot dog.

FIG. 1 shows the overall construction of a dog-shaped robot (or "robot dog") equipped with an olfactory sense. The robot dog 1 has an olfactory ability based on an IMS (Ion Mobility Spectrometry)-type sensor, and by comparing the output of the IMS sensor with a chemical substance database and also communicating with a plurality of other robot dogs, is capable of specifying and analyzing a target chemical substance and tracking and/or chasing after a moving body (criminal). Note that the olfactory sense is defined as one of the senses and is realized by receiving molecules of specified chemical substances at receptors. Accordingly, although the detection of chemical substances included in the atmosphere (external air) or the like is described below as the "olfactory sense" or "odors/smells", in the system (apparatus or robot) described below, it is also possible to detect chemical substances that cannot be detected by animals as an odor.

Smells and odors are caused by chemical substances such as compounds and gases included in air in the periphery, surrounding or environment. In the present specification, the expression "chemical substance" includes compounds, molecules, and elements, and includes products without being limited to constituents or compositions. The expression "chemical substances" also includes organic and inorganic substances. It is said that many chemical substances capable of being detected by the olfactory sense include functional groups. One functional group is hydrocarbons, with an example of such being alkanes (chained saturated hydrocarbons). This group includes ethane, methane, propane, butane, and the like as chemical substances. The functional groups are not limited to hydrocarbon groups, and the amino group and the like can be given as an example of a functional group containing nitrogen and the alcohol group and the ketone group can be given as examples of functional groups that contain oxygen. These are mere examples of chemical substances and functional groups. It is supposed that the atoms in molecules of a functional group are subject to the same or similar chemical reactions and exhibit a characteristic in having a common odor. Volatile organic materials and organic compounds typically stimulate the olfactory sense as odors. The chemical substances may be gases (i.e., a gas itself) such as carbon monoxide or carbon dioxide. The chemical substances may also be inorganic substances, such as carbon, aluminum, or nitrogen.

One analyzer that is compact, portable, and capable of detecting the causes of an odor is the ion mobility sensor described earlier, which has been provided as a chip-type device using MEMS. An ion mobility sensor (or "ion mobility spectrometer") ionizes substances (molecules) present in the air and outputs a spectrum (output pattern or air quality pattern) based on differences in mobility between the ionized molecules, with field asymmetric waveform ion mobility spectrometry (FAIMS) and differential ion mobility spectrometry (DIMS) being known.

A spectrometry-type sensor of this type, hereinafter referred to in general as an "IMS sensor", inputs ionized molecular flows into an asymmetric electric field that changes from low voltage to high voltage and outputs the result of filtering such flows based on field mobility of the ions. The "micro DMx" made by SIONEX and the FAIMS device made by OWLSTONE can be given as examples of compact IMS sensors that are commercially available.

In an IMS sensor, as information relating to chemical substances included in a fluid (typically a carrier gas such as air or nitrogen gas), it is possible to detect an ion current that changes in accordance with the two variables of the voltage Vd (dispersion voltage or electric field voltage (Vrf), alternating current) and the voltage Vc (compensation voltage, direct current). Accordingly, three-dimensional data (waveform data, spectra) including such information and two-dimensional spectra where one of the parameters in three dimensions is fixed are obtained as information relating to chemical substances. It is also possible to acquire spectral features (a spectral signature, spectral characteristics and features) that show the elements of a spectrum as information related to chemical substances. As examples, the spectral features include a spectral peak amplitude, spectral peak width and spectral peak slope, spectral peak interval, number of spectral peaks, relative positional shift of spectral peaks due to changes in processing conditions, spectral discontinuity points, a Vcomp to Vrf characteristic, and the like.

The detection unit (sensor) that obtains information related to the chemical substances may be a mass spectrometry-type sensor so that M/Z (mass-to-charge) is obtained as the information related to the chemical substances included in the fluid.

A spectrometric sensor that uses ion mobility or the like has widespread applicability compared to a sensor that is sensitive to specific constituents (chemical substances) and is capable of detecting the presence and intensity (concentration) of almost all constituents with a similar level of precision in the range where analysis is possible. The information on chemical constituents (chemical substances) detected by the sensor includes intensity variations (which include concentration variations, presence variations, and other changes and variations detected by the sensor) of chemical substances (which includes at least one of compounds, molecules, and elements).

As examples of the sensor that acquires information related to chemical substances, there are a wide variety of sensors including a chemical sensor that conforms to IEEE 1451, a quartz sensor (QCM (Quartz Crystal Microbalance)), an electrochemical sensor, a SAW (Surface Acoustic Wave) device, an optical sensor, gas chromatography, liquid chromatography, and a MOS (Metal Oxide Semiconductor) sensor.

The information (chemical substance-related information) relating to the chemical substances outputted from the sensor will differ according to the type of sensor for detecting the chemical substances, and in many cases different types of chemical substance-related information will be outputted for the same chemical substance. It is important to normally handle such chemical substance-related information of different types in a unified way, for example, by mapping the information of different types onto a space showing chemical substances. However, a certain amount of processing time is required to process different types of chemical substance-related information in a unified way.

In the present specification, chemical substance-related information that is unique to a sensor and has been obtained from different types of sensor is indicated by appending the name of the sensor type. For example, the chemical substance-related information obtained by an IMS sensor is referred to as "IMS data". Also, chemical substance-related information that has been processed such as by mapping chemical substance-related information that is unique to a sensor onto the same space showing chemical substances and can therefore be handled in a unified or generalized manner is referred to as "universal" or "general-purpose" data. One example of universal data is FCWS data proposed by the applicant of the present application. Such data is produced by mapping (assigning) chemical substance-related information that is unique to a sensor to a frequency space that is a space that is characterized to chemical substances according to FCWS (Functionally (i.e., Functional Group) Classification Wave Shaping) technology to convert intensity information showing the presence of chemical substances to intensity information on frequency bands.

When broadly divided, this robot dog 1 includes, a head portion 2, a neck portion 3, a trunk portion 4, a leg portion 5, a rump portion 6, and a tail portion 7. The robot dog 1 includes an internal bus that passes through the head portion 2, the neck portion 3, the trunk portion 4, and the rump portion 6 to reach the tail portion 7 and distributes data and power, so that the various functions (functional units) incorporated in the robot dog 1 are capable of communicating with one another. A battery 8 is housed in the trunk portion 4 so that the robot dog 1 is capable of moving freely on its own. In addition, the robot dog 1 is equipped with various external communication units so that the robot dog 1 is capable of communicating with other robot dogs, a host apparatus, and with various resources that are capable of being accessed via a computer network.

Note that although the following explanation describes a case where units equipped with various functions are housed in the robot dog 1, the locations at which such units are housed are not limited to the locations in the following description. Also, such functions (functional units) are typically realized by software and programmable hardware resources including one or a plurality of CPUs and memory. Such programmable hardware resources may include a chip such as a dedicated ASIC and may include a chip on which circuits are reconfigurable. In addition, although an example where functions relating to the present invention are incorporated in a robot that is a movable, programmable mechanical apparatus is shown, in an application where autonomous mobility is not required, the functions described below can also be realized using a computer including hardware resources like a CPU and memory, such as a terminal (a personal computer, a PDA, or a mobile phone or the like).

First, the robot dog 1 is equipped with an olfactory system 300 including the detection unit 100, the event output unit 30, and the threat monitoring unit 40. The detection unit 100 detects information of chemical-substance relations relating to chemical substances included in a fluid (in the present embodiment, external air 19) at a plurality of sampling points. In the present embodiment, the detection unit 100 includes an IMS sensor and is sometimes referred to hereinafter as the "IMS unit". The event output unit 30 determines (estimates) and outputs the occurrence of an event and the occurrence cause of the event from a change in the chemical substance-related information obtained at the respective sampling points. The threat monitoring unit 40 operates in parallel with the event output unit 30. If a chemical substance that poses a threat or the occurrence cause of an event poses a threat, alarm information that can be recognized by at least one of visually and audibly, for example, a warning by way of sound or light, may be outputted by an alarm issuing unit 59.

The chemical substance-related information handled by the olfactory system 300 is information that changes (varies) according to the presence of chemical substances. At the detection unit 100, information including a spectrum and/or spectral features is outputted as described above as IMS data 115. With this robot dog 1, the left and right nostrils 12L and 12R of the nose 11 on the front surface 10 of the head portion 2 are sampling holes and the detection unit 100 is housed behind the nose 11.

As an overview of the other functions of the robot dog 1, first the robot dog 1 includes a moving unit 500 capable of moving the robot dog 1 in a freely chosen direction by moving the leg portion 5. Using a central control unit (CCU) 55, it is possible to have the robot dog 1 turn and move in the occurrence direction of an event obtained by the event output unit 30.

The robot dog 1 further includes the appended information acquisition unit 60 that acquires event appended information 69 including at least one of images and sound for the occurrence direction of an event, the location of this robot, the bearing of the occurrence direction, a movement direction of the fluid, and environmental data around or on the periphery of this robot. The robot dog 1 includes image acquisition units 61L and 61R that acquire left and right images at the positions of the left and right eyes on the head portion 2. The image acquisition units 61L and 61R are capable of obtaining not only three-dimensional images in the range of visible light but are also capable of obtaining three-dimensional images in the range of infrared light and are therefore able to see in the dark. The image acquisition units 61L and 61R may also be provided with other abilities including the ability to measure distance. The robot dog 1 also includes microphones 62L and 62R that acquire left and right sound (i.e., stereo sound) at the positions of the left and right ears 13 on the head portion 2. The robot dog 1 is capable of moving the head portion 2 up, down, to the left, and to the right relative to the trunk portion 4 by way of an actuator 15 provided in the neck portion 3. Accordingly, by orienting the head portion 2 in the event occurrence direction, it is possible to obtain images and sounds in the event occurrence direction.

In addition, the robot dog 1 includes a GPS unit 63 and is capable of including a global position of the robot dog 1 in the event appended information 69. The robot dog 1 includes an environment measuring unit 64 that includes wind direction, temperature, and humidity, and is capable of including such information in the event appended information 69.

The robot dog 1 further includes various types of communication unit 200, 201, and 210 that transfer event information including the occurrence of an event to the periphery. First, the tail portion 7 of the robot dog 1 forms the RF communication unit 200 that uses the FM and AM frequency bands. The left and right ears 13 form a MIMO-type communication unit 201 for transmitting and receiving large amounts of information. In addition, the nose 11 forms a directional communication interface 211, with a directional communication unit 210 being housed behind the nose 11. The directional communication interface 211 includes a laser communication-type semiconductor laser, a visible light communication LED, a light-receiving unit, an ultrasound emitting apparatus for ultrasonic communication, and a microphone. By moving the actuator 15 of the neck portion 3, it is possible to point the directional communication interface 211 in a desired direction and limit the range of communication, which facilitates improvement in communication precision. It also makes it easier to keep the information being exchanged secret.

Via such communication units 200, 201, and 210, it is possible to access a computer network, such as an intranet or the Internet. Accordingly, the robot dog 1 is capable of using a variety of resources that are available on a computer network. As one example, it is possible to send the IMS data 115 via a computer network to a cause determining server and to obtain the occurrence cause of the event using external resources. Since it is possible via the communication units 200, 201, and 210 to use external resources to estimate the occurrence cause, it is possible to improve the estimation precision for the occurrence cause.

Also, by using the communication units 200, 201, and 210, the robot dog 1 exchanges information with other robot dogs to specify the source of an event through cooperative operation and when the source of an event poses a threat, it is possible to confront such threat. By sharing information on the event occurrence direction with a plurality of robot dogs 1, it is possible to precisely specify the source of the event. Also, if the source of an event moves, it is possible to track such movement or to surround the source.

The robot dog 1 further includes an odor output unit 400 that releases chemical substances that are a source of a specified odor. By placing an odor that can identify the robot dog 1 at a specified target location during movement, it becomes possible to cause a robot dog 1 equipped with the same functions to track the present robot dog 1. By using an unnoticeable odor that humans are incapable of recognizing or an odor that is not distinctive enough to be distinguished from background odor, it is possible to indirectly inform other robot dogs 1 of the movement path or the like of the robot dog 1.

Figure 2:
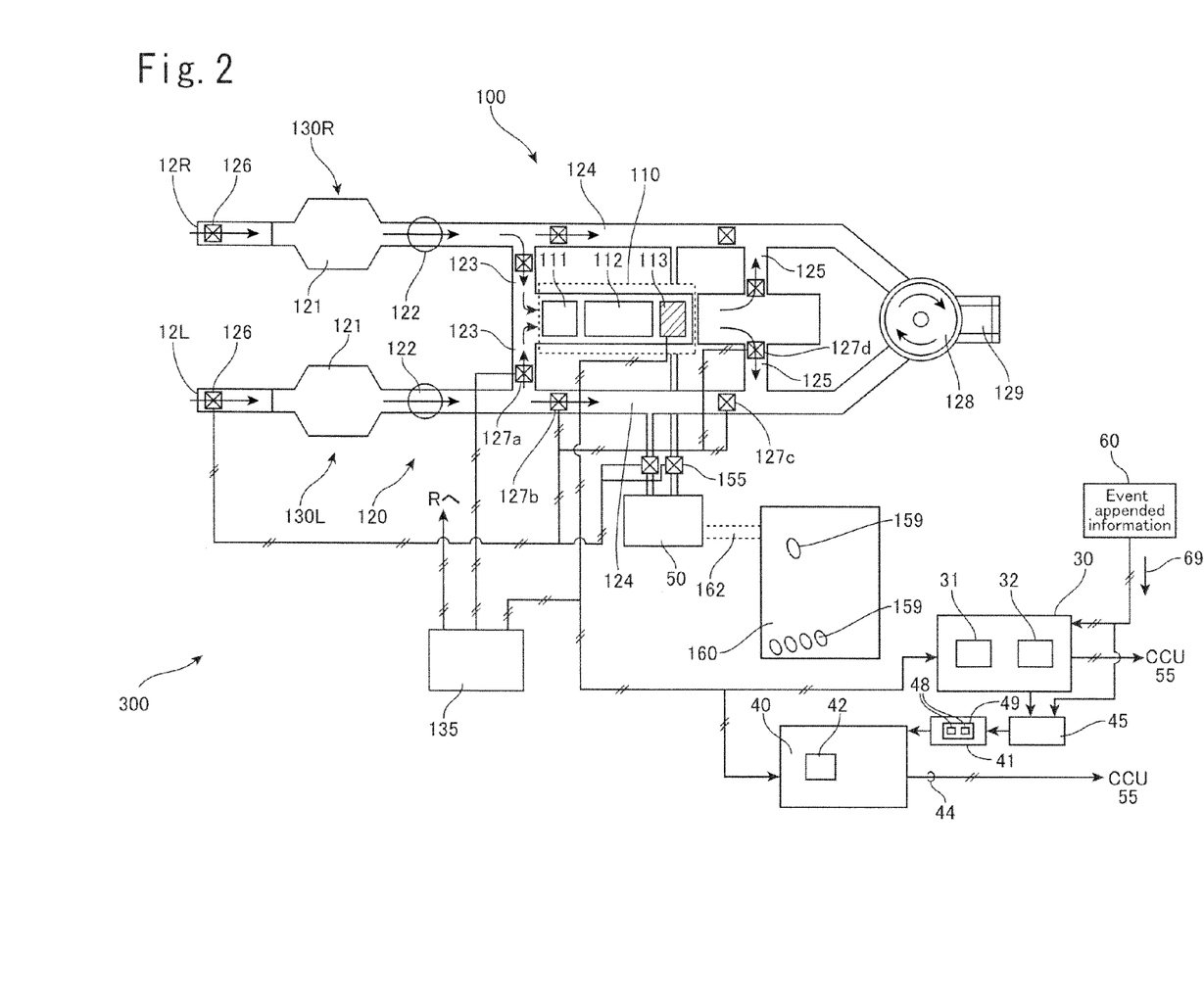
FIG. 2 is a block diagram showing an olfactory system.

FIG. 2 is a block diagram showing the outlines of the olfactory system 300. The olfactory system 300 includes the detection unit 100 that acquires chemical substance-related information relating to chemical substances included in the external air 19 at a sampling point using a first type of sensor, in the present embodiment, the IMS sensor 110, a local memory 41 storing a library 49 including specifying patterns 48 that are patterns generated when specified chemical substances were detected by the IMS sensor 110 respectively, and the threat monitoring unit 40 that routinely compares the chemical substance-related data (IMS data) 115 obtained by the detection unit 100 with the specifying patterns 48 for monitoring purposes included in the library 41. The threat monitoring unit 40 includes a matching unit (collation unit) 42 that outputs match information when the obtained IMS data 115 and any of the specifying patterns 48 for monitoring purposes match.

A specifying pattern 48 includes spectral features (a spectral signature, spectral characteristics, and features) showing the elements in an output spectrum of the IMS sensor 110 included in the IMS data 115. The spectral features include a spectral peak amplitude, spectral peak width and spectral peak slope, spectral peak interval, number of spectral peaks, relative positional shift of spectral peaks due to changes in processing conditions, spectral discontinuity points, a Vcomp to Vrf characteristic, and the like, but are not limited to such.

The matching unit 42 may extract a number of parameters corresponding to the spectral features of the specifying patterns 48 from the output spectrum included in the IMS data 115 and match or check such parameters against the spectral features in the library 49. Also, the matching unit 42 may synthesize spectra for matching purposes from the spectral features in the library 49 and match the specifying patterns 48 and the IMS data 115 using a technique such as pattern matching.

The olfactory system 300 further includes the event output unit 30 that outputs an event occurrence and an occurrence cause of the event from a change in the obtained IMS data (chemical substance-related data) 115, and the matching unit 42 operates with the event output unit 30 according to time division (time sharing) or in parallel. The olfactory system 300 also includes an automated updating unit 45 that automatically updates the specifying patterns 48 stored in the library 49 in the local memory 41 via the communication unit 200 (the other communication units 201 or 210 may also be used, but the communication unit 200 is used as a representative example in the following description). The olfactory system 300 also includes a sample storage unit 50 that seals the external air 19 acquired from a sampling point in a sample storage capsule 159.

First, the detection unit 100 includes an IMS sensor 110 that is shared by the left and right nostrils 12L and 12R. The detection unit 100 includes the IMS sensor 110 that is shared between the plurality of sampling points 12R and 12L, the supply unit 120 that supplies fluid (in the present embodiment, air (external air)) 19 from the plurality of sampling points 12R and 12L to the IMS sensor 110 according to time division, and the sample storage unit 50 that is capable of sealing and storing the external air 19 in a sample storage capsule 159. The IMS sensor 110 may be installed separately at the left and right nostrils 12L and 12R.

The IMS sensor 110 includes an ionizing unit 111 that ionizes the chemical substances included in the drawn-in external air 19 using radiation, light, an electric field, or the like, an electric field control filter 112 that controls the movement of the ionized chemical substances, and a unit 113 that outputs IMS data 115 as information relating to the chemical substances included in the external air 19 from the movement amounts of the ionized chemical substances.

The supply unit 120 includes a suction fan (suction pump) 128 for drawing in the external air 19 from the left and right nostrils 12L and 12R that are the sampling points and discharging the external air 19 from a discharge outlet 129 and ducts 130L and 130R that lead the external air 19 from the left and right nostrils 12L and 12R to the IMS sensor 110 according to time division. The left and right ducts 130L and 130R have the same construction and each include a suction chamber 121, a flexible connector 122, a supply tube 123 that supplies the external air 19 to the IMS sensor 110, a bypass tube 124 that bypasses the supply tube 123, and an exhaust tube 125 for exhausting air from the IMS sensor 110. The movable (flexible) connector 122 is provided to change the orientation of the left and right nostrils 12L and 12R of the nose that are the sampling points by around ±15° (this is not a limitation) in the up, down, left, and right directions. Accordingly, it is possible to change the orientation of the sampling points 12L and 12R without moving the neck portion 3.

A shutoff damper 126 is provided in each of the left and right nostrils 12L and 12R and is capable of shutting off the detection unit 100 from the external air 19. Dampers 127a to 127d are provided on the supply tube 123, the bypass tube 124, and the discharge tube 125 so that such tubes can be separated. The detection unit 100 further includes a control unit 135 that controls such dampers 126 and 127a to 127d and the IMS sensor 110.

For example, when drawing in and analyzing the external air 19 from the left nostril 12L, the dampers 127a to 127d of the right duct 130R are closed and the dampers 127a to 127d of the left duct 130L are opened to purge the lines. Next, the dampers 127a to 127d of the right duct 130R are closed and the chemical substances included in the external air 19 drawn in from the left nostril 12L are detected by the IMS sensor 110. The IMS data 115 is supplied to the event output unit 30 and the threat monitoring unit 40.

If an event and a threat have not been detected at the event output unit 30 and the threat monitoring unit 40, air is drawn in and analyzed in the same way as described above from the right nostril 12R.

If an event has been detected by the event output unit 30 but the event cause cannot be inferred, there is the possibility that the chemical substances included in the external air 19 are unconfirmed or are substances for which there is no analysis record at the IMS sensor 110. Accordingly, before advancing to analysis of the right nostril 12R, the control unit 135 opens the damper 155 that had shut off the bypass tube 124 and the sample storage unit 50 and has the external air 19 accumulated in the bypass tube 124 sealed by the sample storage unit 50 in a sample storage capsule 159. The capsule is then stored via a capsule discharging route 162 in a stocker 160. The external air 19 sealed in the sample storage capsule 159 stocked in the stocker 160 is subsequently analyzed using an IMS sensor 110 of the same type and a high-precision mass analyzer or the like of a suitable type and is then added to a chemical substance database. By executing this type of process, it is possible to subsequently analyze chemical substances that the IMS sensor 110 provided in the robot was unable to analyze at the time of sampling.

The sample storage unit 50 may automatically store a sample in the capsule 159 as described above or may store a sample in a capsule 159 according to an instruction (remote instruction) from the user. For example, it is possible to regularly confirm the functioning of the detection unit 100 and/or to regularly sample the environment in which the robot dog 1 is placed and to store the results as a historical record.

The event output unit 30 includes an event monitoring unit 31 that determines or finds the cause of an event according to changes in the IMS data 115 of the external air 19 sampled at the respective left and right sampling points 12L and 12R and also a cause estimating unit 32. A change in the IMS data 115 that is chemical substance-related information implies at least one of a change in the chemical substances and a change in the concentration of the chemical substances included in the external air 19 at the sampling points 12L and 12R. The event monitoring unit 31 compares the IMS data 115 for the previous sampling and the IMS data 115 for the present sampling and determines that an event has occurred when the difference exceeds a threshold set in advance in the event monitoring unit 31.

The "event" in such a case includes various situations such as the releasing of a new chemical substance to the external air 19 and the releasing of a large amount of chemical substances into the external air 19. Examples of events include the placement of something with an odor, the appearance of something accompanied by an odor, and an event that is accompanied by an odor. Here, the expression "odor (smell)" is not limited to odors that can be felt by humans and may include chemical substances included in the external air 19 with a concentration that can be detected by the IMS sensor 110. The expression "something accompanied by an odor" includes dangerous substances such as pollutants, explosives, and narcotics, and living creatures such as humans. The expression "event that is accompanied by an odor" includes a shooting and a fire.

In addition, the event output unit 30 determines the occurrence direction of an event relative to the robot dog 1. The event output unit 30 is capable of determining the occurrence direction of an event by acquiring stereo-type chemical substance detection information. From the time difference and/or concentration difference between the chemical substances detected at the plurality of sampling points and the three-dimensional positional relationship between the plurality of sampling points, it is possible to determine (estimate) the occurrence direction of the event. With the robot dog 1, although the left and right nostrils 12L and 12R of the noise are used as the sampling points, it is also possible to provide sampling points at more distant positions. For example, by setting or adding the holes of the ears 13 as sampling points, it is possible to improve the precision for the event occurrence direction in the up-down direction.

The positions where sampling points are provided to detect chemical substances are not limited to the head portion 2 and may be provided at other locations, such as by being provided on the trunk portion 4 or being provided on the rump portion 6, for example. Also, the substance detection unit 100 provided on the robot dog 1 is not limited to a single unit and units may be separately provided on the head portion 2, the trunk portion 4, and the rump portion 6.

The cause estimating unit 32 includes a database storing a variety of patterns corresponding to the IMS data 115 and is capable of analyzing the IMS data 115 using an analysis technique such as pattern matching and estimating the cause of the IMS data 115 or of changes thereto. Also, the cause estimating unit 32 may obtain the occurrence cause or causes of an event by sending the IMS data 115 via the communication unit 200 to external hardware resources, for example, an analysis server. The robot dog 1 is capable of approaching the source of an event and of acquiring IMS data 115 corresponding to chemical substances of a higher concentration. Accordingly, it is possible to improve the estimation precision of the occurrence cause of an event.

In addition, the cause estimating unit 32 improves the estimation precision of the event causes by using the event appended information 69 such as images and sound in the event direction that can be acquired by the appended information acquisition unit 60. It is also possible to limit the search range of a pattern for a search in the IMS data 115 using the event appended information 69 such as images and sound and thereby reduce the processing time for estimating the cause of an event.

The threat monitoring unit 40 operates in parallel with the event output unit 30. If the functions as the event output unit 30 and the functions as the threat monitoring unit 40 are realized by a shared processor (CPU), the shared processor may be used according to time division. Also, if the event output unit 30 and the threat monitoring unit 40 are mounted in a chip with reconfigurable hardware, if there are sufficient resources, such units may be mounted so as to operate in parallel, but if there are insufficient resources, such units may be mounted so as to operate according to time division.

The threat monitoring unit 40 includes the local memory 41 that stores the library 49 including specifying patterns 48 that are information having directly comparable elements of chemical substances to be searched with the IMS data 115 and/or a plurality of characteristic parameters (spectral features) for facilitate matching produced by converting (reverse converting) the directly comparable information, and the matching unit (collation unit) 42 that routinely matches the specifying patterns 48 and the IMS data 115 according to an analysis technique such as pattern matching. A typical example of information that can be directly compared or matched against the IMS data 115 is data (IMS data) produced or generated by the IMS sensor 110 detecting the chemical substance that is the search target or an odor (smell) from the search target itself. On determining or judging that a specifying pattern 48 and the IMS data 115 match, or that a specifying pattern 48 is included in the IMS data 115, the matching unit 42 outputs match information 44 and takes a countermeasure such as outputting an alarm.

Representative examples of targets for which specifying patterns 48 are stored in a continuous search library 49 and are subjected to routine or continuous searches (monitoring) are toxic substances that pose a threat to humans, explosives, weapons, drugs such as illegal narcotics, criminals who are being tracked, and missing persons. By storing the IMS data 115 outputted when the IMS sensor 110 has detected the unique odors of such search targets in advance in the local memory 41, it is possible for the robot dog 1 to find the search targets in a shorter time and much more effectively.

The number of types or varieties of chemical substances that pose a threat that needs to be immediately detected is not so large. It is also possible to narrow down the causes of threats that can be confronted by the robot dog 1 according to the mobilization objective, location, and the like of the robot dog 1. On the other hand, when detection needs to be immediate, the processing time required to compare outputs that differ according to the type of sensor for detecting the chemical substances (in the present embodiment, the IMS-type sensor 110) with the universal database is potentially fatal.

In this olfactory system 300, the library 49 that stores specifying patterns 48 which can be directly compared with the output (IMS data 115) of the IMS sensor 110 used to detect chemical substances or can be compared by merely extracting features is stored in the local memory 41, such as a cache memory, which has a short access time. Accordingly, by referring to the library 49, it is possible for the matching unit 42 to determine the risk of a threat occurring in a short time. Also, by limiting the number of specifying patterns 48 stored in the library 49, it is possible to store the specifying patterns 48 in the library 49 with a data format that facilitates comparison with the IMS data 115.

For example, by providing uncompressed specifying patterns 48 in the library 49, it is possible to omit the time required for decompression. In addition, since it is possible to reduce the time and resources required for the processing of the matching unit 42, it becomes easier to carry out parallel processing or time-division processing with the other processes such as the process of the cause estimating unit 32 or the like. Accordingly, it is possible for the threat monitoring unit 40 to routinely determine the risk of the presence of a threat in a short time.

The automated updating unit 45 automatically replaces the specifying patterns 48 stored in the library 49 for continuous monitoring. The automated updating unit 45 is capable of updating the specifying patterns 48 in the library 49 based on the occurrence cause of the event acquired by the event output unit 30. The automated updating unit 45 is capable of determining or interpreting the current state from the event occurrence cause and/or from images and/or sound around the apparatus included in the event appended information 69 and also the images, sound, and the like in the event occurrence direction and of updating the specifying patterns 48 in the library 49. When a unit that acquires the other event appended information is also included, the automated updating unit 45 is capable of updating the specifying patterns 48 based on the other event appended information.

By updating the specifying patterns 48 stored in the library 49 based on the state facing the robot dog 1, it is possible to detect threats much more reliably. Also, by automatically updating the specifying patterns 48 stored in the library 49, it becomes possible to limit to a certain degree the amount of specifying patterns 48 stored in the library 49. Accordingly, the time required to search for threats can be further reduced.

For example, if one chemical substance included in the specifying patterns 48 has been recognized, it is possible to automatically update the specifying patterns 48 so as to include other chemical substances that can pose a danger by causing a chemical reaction with the recognized chemical substance, reactive elements for which the reactive energy or heat is extremely dangerous, and the like in the specifying patterns 48. Also, if one chemical substance included in the specifying patterns 48 has been recognized (matched) and an increase in the proportion of such chemical substance carries the risk of a dangerous chemical reaction occurring, it is possible to update the specifying patterns 48 so as to frequently check the concentration of such chemical substance.

Figure 3:
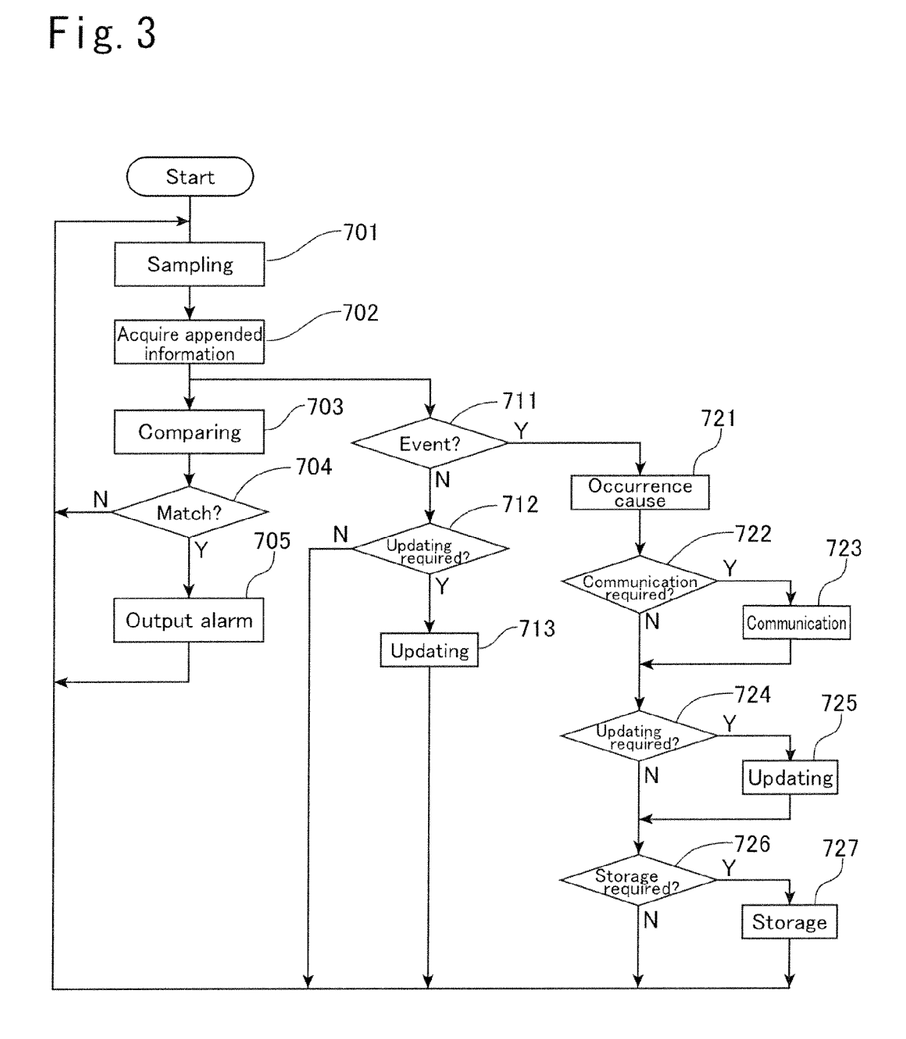
FIG. 3 is a flowchart showing the overall control of the olfactory system.

FIG. 3 shows typical control of the olfactory system 300 by way of a flowchart. Such control can be provided via a computer network or recorded on a recording medium as a program (program product).

In step 701, the IMS sensor 110 of the detection unit 100 carries out sampling at a plurality of sampling points and outputs the IMS data 115. Before or after such process or in parallel with it, in step 702 the appended information acquisition unit 60 acquires the appended information 69.

In step 703, the IMS data 115 obtained by sampling and the specifying patterns 48 for monitoring purposes included in the library 49 of the local memory 41 are routinely compared and matched by the threat monitoring unit 40. If, in step 704, the IMS data 115 and a specifying pattern 48 for monitoring purposes match, in step 705 the match information 44 is outputted. In step 705, since a threat has been discovered, this normally leads to an alarm output. As described above, the processing load of the threat monitoring unit 40 is low. Accordingly, such processing may be assigned to part of the processing ability of the central control unit 55 that includes a CPU and memory, a dedicated processor may be provided, or a processing system that carries out a number of jobs including monitoring threats in parallel may be provided.

Also, in parallel or according to time division with the threat monitoring process described above, in step 711 the event output unit 30 checks for the occurrence of an event from (using, based on) changes in the IMS data 115. If, in parallel with or before and after the checking for an event, the automated updating unit 45 determines or finds in step 712 that it is necessary to update the specifying patterns 48 based on the event appended information 69, in step 713 the specifying patterns 48 are updated. It is possible to update the specifying patterns 48 in keeping with the location and state being monitored by the robot dog 1.

If an event has been detected in step 711, in step 721 the cause estimating unit 32 determines the occurrence cause of the event based on the IMS data 115. If the central control unit 55 determines in step 722 that support is required from resources such as an external server, in step 723 the event information is transmitted together with the event appended information via the communication unit 200 and the like to the outside. Via the communication unit 200, the event occurrence information including the obtained IMS data 115 may be transferred and the occurrence cause or causes of the event may be acquired from an external server or the like.

On determining in step 724 that it is necessary to update the specifying patterns 48 based on the occurrence cause or causes of the event, in step 725 the automated updating unit 45 automatically updates the specifying patterns 48 stored in the library 49 of the local memory 41 via the communication unit 200. The specifying patterns 48 to be updated may be provided via the communication unit 200 together with the event occurrence cause from the external server or a controller or the like of the robot dog 1.

If, in step 726, the event occurrence cause has not been established, in step 727 the central control unit 55 has the fluid at the sampling point sealed in a sample storage capsule 159 by the sample storage unit 50.

In this way, one characteristic of the olfactory robot dog 1 is that the dog is configured to give priority to carrying out processing that are extremely dangerous and/or poisons, such as explosive substances, poisonous gas, and harmful substances, so that it is possible to react to an emergency by stopping all analysis and carrying out the prioritized processing.

In addition, the robot dog 1 is equipped with the threat monitoring unit 40 that functions independently as a dedicated danger predicting unit and continuously monitors conditions that can pose a threat. When a chemical substance database for search targets of the present robot dog 1 has been loaded into the local memory 41 but an unregistered chemical substance has been encountered, it is possible to refer to remotely-located global data either independently or via the cause estimating unit 32.

The olfactory robot dog 1 is capable of switching between a plurality of modes according to instructions from a controller. The threat monitoring unit 40 can be used when analyzing chemical substances that are search targets and substances of the same system, and by having a search database (library) 49 in the local memory 41 of the robot dog 1, it is possible for the matching unit 42 to refer to the database in a short time. The database 49 uses an RD structure where it is possible to search using a plurality of keys, and it is possible to use a construction where similar chemical substances, intermediate reactants that are susceptible to chemical changes, and byproducts or the like are disposed short distances apart in the search space.

In addition, if there is no registration in the global data, the robot dog 1 is capable via the sample storage unit 50 of registering a substance as a new chemical substance. That is, if a cause cannot be determined, instead of having the external air 19 simply discharged from the substance detection unit 100, the external air is switched to the sample storage unit 50 and is stored in a capsule 159. By doing so and matching against the analysis results of an existing analyzing apparatus at a later time and subsequently registering the result, it is possible to improve the quality of the database used to supply the specifying patterns 48 used to determine threats. To construct a vast database including the specifying patterns 48 with appropriate quality, such an automated system is extremely important. To efficiently enhance or construct a database for an IMS sensor, it is preferable to build rules for matching the difference data produced when analysis results of existing mass spectrometry apparatuses and the like are compared with analysis results using IMS or for absorbing and compensating for such differences. By accumulating statistical data in this way, the building of a database including the automatic generation of specifying patterns for an IMS sensor can be automated.

If a new chemical substance has been detected, the olfactory robot dog 1 may provisionally register the substance via a network in a global memory. With this method, if the substance is later specified by carrying out component analysis, proper registration is carried out. A signature of the chemical substance is registered and substances are estimated using a given estimation algorithm. Such estimation uses an arrangement where the algorithm and estimation reasoning (rules) are modified to improve the accuracy using statistical processing and the results of specifying actual substances. This is referred to as the estimation and learning of chemical substances and contributes to reducing the time required for humans to specify chemical substances. In other words, this contributes to advancing from a semi-automated algorithm to a fully automated algorithm. To increase the estimation accuracy and learning efficiency, it is extremely important to discover not only the signature information of the search target but also other information at such location, such as humidity and temperature and factors that fall into the gap between actual analysis results and analogizing including correlation with other signatures present at such location.

Note that although the olfactory system 300 mounted in the robot dog 1 has been described above as an example of a robot that is capable of moving independently, the olfactory system 300 may be mounted in a movable apparatus such as another type of robot or a mobile terminal or the like (which includes mobile phones), or in an apparatus that is fixed. Also, although the olfactory system 300 described above includes a plurality of sampling points, the system may detect chemical substances included in external air 19 collected at a single sampling point.

Also, although the robot dog 1 is one example of a robot capable of moving on the ground, the robot may be a robot bird or a robot that is capable of floating or flying in the air. In addition, the robot may be a robot that moves over or under the sea. Also, although a robot including a function that detects chemical substances present in a gas has been described above as an example, the robot may include a function that detects chemical substances included in water or in the sea. In addition, the function for monitoring threats may be mounted in a mobile information terminal together with the IMS sensor 110 and the like, may be mounted in a moving body such as a car, an airplane, or a boat, may be mounted in a domestic appliance, and/or may be mounted in a security product for protecting a home or other kind of building.

The invention claimed is:

1. An apparatus comprising:
 a detection unit acquiring chemical substance-related information relating to a chemical substance included in a fluid at a sampling point using a spectrometric sensor;
 a communication unit that communicates wirelessly or via wires with an outside device;
 a local memory storing a threat detection library including a specifying pattern generated when a specified chemical substance that is a cause of a threat was detected by the spectrometric sensor; and
 a processor that includes a matching process and an outputting process and executes, in parallel or according to time division, the matching process and the outputting process,
 wherein the matching process routinely compares chemical substance-related information obtained by the detection unit and a specifying pattern for monitoring purposes included in the threat detection library, and outputs match information when the obtained chemical substance-related information and the specifying pattern for monitoring purposes match, and
 wherein the outputting process determines that an event relating to an odor has occurred based on a change in a chemical constituent or a change in concentration of detected chemical substances included in the obtained chemical substance-related information and outputs an occurrence of an event and an occurrence cause of the event, the outputting process including transferring, via the communication unit, the chemical substance-related information to the outside device and obtaining the occurrence cause of the event that includes chemical substances estimated from the chemical substance-related information and/or a cause of outputting of the estimated chemical substances.

2. The apparatus according to claim 1, wherein the processor includes a function that acquires a specifying pattern of a chemical substance that poses a threat based on the occurrence cause of the event via the communication unit and updates the threat detection library in the local memory using the acquired specifying pattern.

3. The apparatus according to claim 1, further comprising a unit that acquires event appended information including images and/or sound around the apparatus, and the processor includes a function that interprets a state based on the images and/or sound included in the event appended information, acquires, via the communication unit, a specifying pattern including elements of an odor that poses a threat in the interpreted state, and updates the threat detection library in the local memory using the acquired specifying pattern.

4. The apparatus according to claim 1, further comprising a sample storing unit operable when the occurrence cause of the event is not established, to seal the fluid at the sampling point in a storage capsule.

5. A method that controls an apparatus including: a detection unit detecting chemical substance-related information relating to a chemical substance included in a fluid at a sampling point using an ion mobility sensor; a communication unit that communicates wirelessly or via wires with an outside device; a local memory storing a threat detection library including a specifying pattern generated when a specified chemical substance that is a cause of a threat was detected by a spectrometric sensor; and a processor, the processor executing: a matching process which routinely compares chemical substance-related information obtained by the detection unit and a specifying pattern for monitoring purposes included in the threat detection library and outputs match information when the obtained chemical substance-related information and the specifying pattern for monitoring purposes match; and in parallel or according to time division with the matching process, a process that determines that an event relating to an odor has occurred based on a change in a chemical constituent or a change in concentration of detected chemical substances included in the obtained chemical substance-related information, and outputs an occurrence of an event and an occurrence cause of the event, the process including transferring, via the communication unit, the chemical substance-related information to the outside device and obtaining the occurrence cause of the event including chemical substances estimated from the chemical substance-related information and/or a cause of outputting of the estimated chemical substances.

6. The method according to claim 5, further comprising the processor acquiring a specifying pattern of a chemical substance that poses a threat based on the occurrence cause of the event via the communication unit and updating the threat detection library in the local memory using the acquired specifying pattern.

7. The method according to claim 5, further comprising the processor acquiring event appended information including images and/or sound around the apparatus, and the processor interpreting a state based on the images and/or sound included in the event appended information, acquiring, via the communication unit, a specifying pattern including elements of an odor that poses a threat in the state, and updating the threat detection library in the local memory using the acquired specifying pattern.

8. A nontransitory computer readable medium encoded with a program executed by an apparatus including: a detection unit detecting chemical substance-related information relating to a chemical substance included in a fluid at a sampling point using a spectrometric sensor; a communication unit that communicates wirelessly or via wires with an outside device; a local memory storing a threat detection library including a specifying pattern generated when a specified chemical substance that is a cause of a threat was detected by the spectrometric sensor; and a processor, the program comprising instructions that have the processor execute: a matching process which routinely compares chemical substance-related information obtained by the detection unit and a specifying pattern for monitoring purposes included in the threat detection library and outputs match information when the obtained chemical substance-related information and the specifying pattern for monitoring purposes match; and, in parallel or according to time division with the matching process, a process that determines that an event relating to an odor has occurred based on a change in a chemical constituent or a change in concentration of detected chemical substances included in the obtained chemical substance-related information, and outputs an occurrence of an event and an occurrence cause of the event, the process including transferring, via the communication unit, the chemical substance-related information to the outside device and obtaining the occurrence cause of the event including chemical substances estimated from the chemical substance-related information and/or a cause of outputting of the estimated chemical substances.

9. The apparatus according to claim 1, wherein the spectrometric sensor is an ion-mobility sensor.

10. The apparatus according to claim 1, wherein the spectrometric sensor is a mass spectrometry sensor.

* * * * *